US012611178B2

(12) United States Patent
Ma et al.

(10) Patent No.: US 12,611,178 B2
(45) Date of Patent: Apr. 28, 2026

(54) ULTRASONIC PROBE AND ULTRASONIC DEVICE INCORPORATING DIFFERENT ARRAYS

(71) Applicant: WUHAN UNITED IMAGING HEALTHCARE CO., LTD., Hubei (CN)

(72) Inventors: Xianglong Ma, Hubei (CN); Kang Si, Hubei (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 0 days.

(21) Appl. No.: 18/909,999

(22) Filed: Oct. 9, 2024

(65) Prior Publication Data

US 2025/0176939 A1     Jun. 5, 2025

(30) Foreign Application Priority Data

Nov. 30, 2023     (CN) .......................... 202311641396.3

(51) Int. Cl.
*A61B 8/00* (2006.01)
*B06B 1/06* (2006.01)

(52) U.S. Cl.
CPC .......... *A61B 8/4494* (2013.01); *A61B 8/4477* (2013.01); *A61B 8/461* (2013.01); *B06B 1/0622* (2013.01); *B06B 2201/76* (2013.01)

(58) Field of Classification Search
CPC ....... A61B 8/12; A61B 8/445; G01S 7/52079; B06B 1/0633
See application file for complete search history.

(56) References Cited

U.S. PATENT DOCUMENTS

2004/0152986 A1*   8/2004   Fidel ........................ A61B 8/12
                                                                        600/459
2004/0168517 A1*   9/2004   Dufait ................... B06B 1/0622
                                                                        73/626

(Continued)

FOREIGN PATENT DOCUMENTS

CN        200942088 Y      9/2007
CN        102415906 A      4/2012

(Continued)

OTHER PUBLICATIONS

CN-110448332-A (Year: 2019).*

(Continued)

*Primary Examiner* — Nyrobi Celestine

(57) ABSTRACT

The present disclosure relates to an ultrasonic probe and an ultrasonic device. The ultrasonic probe includes a linear array and two convex arrays arranged on both sides of the linear array in a first direction. An inner wall of a cavity and tissues close to the inner wall of the cavity are detected by the convex arrays to obtain a coronal plane image. A position of a puncture needle can be detected by the linear array to obtain a sagittal plane image. The convex arrays and the linear array transmit and receive ultrasonic waves simultaneously during use, so that the positions of the punctured tissue and the tip of the puncture needle can be observed simultaneously, without the need for frequently moving the ultrasonic probe to switch between two planes, thereby accurately achieving the intracavitary puncture operation and improving the detection accuracy and efficiency.

20 Claims, 9 Drawing Sheets

(56)            References Cited

U.S. PATENT DOCUMENTS

| | | | | |
|---|---|---|---|---|
| 2007/0167752 | A1* | 7/2007 | Proulx | G01S 15/8925 |
| | | | | 600/437 |
| 2012/0143063 | A1 | 6/2012 | Robinson | |
| 2016/0338675 | A1* | 11/2016 | Kubota | A61B 17/3403 |
| 2019/0099163 | A1* | 4/2019 | Morimoto | A61B 8/546 |
| 2022/0218308 | A1 | 7/2022 | Oh | |
| 2023/0386040 | A1* | 11/2023 | Li | G06T 7/62 |
| 2024/0050067 | A1* | 2/2024 | Sasaki | A61B 8/0841 |

FOREIGN PATENT DOCUMENTS

| | | | | | |
|---|---|---|---|---|---|
| CN | 209059260 | U | | 7/2019 | |
| CN | 110448332 | A | * | 11/2019 | A61B 8/4483 |
| CN | 114668422 | A | | 6/2022 | |
| CN | 217219063 | U | | 8/2022 | |
| CN | 117530720 | A | | 2/2024 | |
| WO | WO-2019116414 | A1 | * | 6/2019 | A61B 8/14 |

OTHER PUBLICATIONS

WO-2019116414-A1 (Year: 2019).*

Extended European Search Report of Counterpart European Patent Application No. 24207078.7 issued on Apr. 4, 2025.

* cited by examiner

ULTRASONIC PROBE AND ULTRASONIC DEVICE INCORPORATING DIFFERENT ARRAYS

CROSS-REFERENCE TO RELATED APPLICATIONS

This application claims priority to Chinese patent application No. 202311641396.3, filed on Nov. 30, 2023, the content of which is hereby incorporated by reference in its entirety.

TECHNICAL FIELD

The present disclosure relates to the field of medical technologies, and in particular, to an ultrasonic probe and an ultrasonic device.

BACKGROUND

Ultrasonic devices are commonly used to scan an object to be detected (such as a certain part of a patient's body) for diagnostic imaging.

Ultrasonic probe is an important component of the ultrasonic device. According to different clinical uses, the ultrasonic probes have many different types. An intracavitary probe is an ultrasonic probe that can be inserted into a cavity of a human organ, which can be used for trans-anorectal, trans-vaginal or trans-esophageal examinations, for example.

Taking the application of the probe in intracavitary ultrasound puncture diagnosis as an example, in the related art, during an insertion of the probe into the cavity, a position of a puncture needle and a position of a punctured tissue cannot be simultaneously presented in an ultrasonic image. Doctors need to frequently move the probe to determine the positions of the punctured tissue and the puncture needle, which affects the detection efficiency.

SUMMARY

Based on this, it is necessary to provide an ultrasonic probe to address the problem of low detection efficiency in conventional ultrasonic probes.

Disclosed is an ultrasonic probe. The ultrasonic probe includes a transducer assembly. The transducer assembly includes a first transducer including two convex arrays arranged in a first direction, and a linear array connected between the two convex arrays. An arrangement direction of the linear array is perpendicular to the first direction.

In an embodiment, a field of view angle of each of the two convex arrays is an obtuse angle.

In an embodiment, the linear array extends a first distance relative to each of the two convex arrays in the arrangement direction of the linear array, and a ratio of the first distance to a length of the linear array is higher than 0 and less than or equal to 2/3.

In an embodiment, the ratio of the first distance to the length of the linear array is higher than or equal to 1/4 and less than or equal to 1/2.

In an embodiment, each of the two convex arrays includes a first lens layer, and the first lens layer has a first bonding surface. The linear array includes a second lens layer, and the second lens layer has second bonding surfaces. Each of the second bonding surfaces is connected to one of the first bonding surfaces.

In an embodiment, an orientation of each of the first bonding surfaces is in conformity with an orientation of one of the second bonding surfaces located on a same side.

In an embodiment, the first bonding surfaces and the second bonding surfaces are each a cambered surface.

In an embodiment, a distance between the first bonding surfaces of the two convex arrays gradually decreases first and then gradually increases in the arrangement direction of the linear array.

In an embodiment, a minimum distance between the two first bonding surfaces is greater than an elevation of the linear array.

In an embodiment, each of the two convex arrays further includes a first piezoelectric layer stacked with the first lens layer in a second direction, and the linear array further includes a second piezoelectric layer stacked with the second lens layer in the second direction. The second direction, the first direction and the arrangement direction of the linear array are perpendicular to each other.

In an embodiment, each of the two convex arrays further includes a first matching layer arranged between the first lens layer and the first piezoelectric layer, and the linear array further includes a second matching layer arranged between the second lens layer and the second piezoelectric layer.

In an embodiment, each of the two convex arrays further includes a first backing layer stacked on a side of the first piezoelectric layer facing away from the first matching layer, and the linear array further includes a second backing layer stacked on a side of the second piezoelectric layer facing away from the second matching layer.

In an embodiment, each of the two convex arrays further includes a first heat dissipation member connected to the first backing layer, and the linear array further includes a second heat dissipation member connected to the second backing layer.

In an embodiment, the first backing layer and the first heat dissipation member are provided with a first concave-convex matching portion and a second concave-convex matching portion configured to engage with the first concave-convex matching portion, respectively, and/or the second backing layer and the second heat dissipation member are provided with a third concave-convex matching portion and a fourth concave-convex matching portion configured to engage with the third concave-convex matching portion, respectively.

In an embodiment, the first heat dissipation member is connected to a side of the first backing layer facing away from the first matching layer, and/or the second heat dissipation member is connected to a side of the second backing layer facing away from the second matching layer.

In an embodiment, the first heat dissipation member is connected to a side of the first backing layer in the first direction, and/or the second heat dissipation member is connected to a side of the second backing layer in the first direction.

In an embodiment, the first lens layer and the second lens layer are in an integrated structure, and/or the two first backing layers are in an integrated structure.

In an embodiment, the ultrasonic probe further includes a connecting member, and the linear array and each of the two convex arrays are each connected to the connecting member.

In an embodiment, the connecting member includes a first support section and second support sections connected to both sides of the first support section in the first direction. The ultrasonic probe further includes a first fastener configured to connect the first support section and the linear array, and the ultrasonic probe further includes a second fastener configured to connect the second support section and one of the convex arrays located on a same side.

In an embodiment, each of the second support sections is slidably connected to the first support section, and is capable of driving one of the two convex arrays to move in the arrangement direction of the linear array.

Disclosed is an ultrasonic device, including a host, a display and an ultrasonic probe as described above. The ultrasonic probe is configured to acquire ultrasonic imaging data. The host is communicatively connected with the ultrasonic probe, and is configured to receive and process the ultrasonic imaging data to generate an ultrasonic image. The display is connected to the host, and is configured to display the ultrasonic image.

The above ultrasonic probe includes one linear array and two convex arrays arranged on both sides of the linear array. An inner wall of a cavity and a tissue close thereto are detected by the convex arrays to obtain a coronal plane image, so that a position of a punctured tissue can be observed. A position of a puncture needle can be detected by the linear array to obtain a sagittal plane image, so that the position of the tip of the puncture needle can be observed. The convex arrays and the linear array transmit and receive simultaneously during use, so that the positions of the punctured tissue and the tip of the puncture needle can be observed simultaneously, without the need for frequently moving the ultrasonic probe to switch between two planes, thereby accurately achieving the intracavitary puncture operations and improving the detection accuracy and efficiency.

REFERENCE NUMBERS

Figure 1:
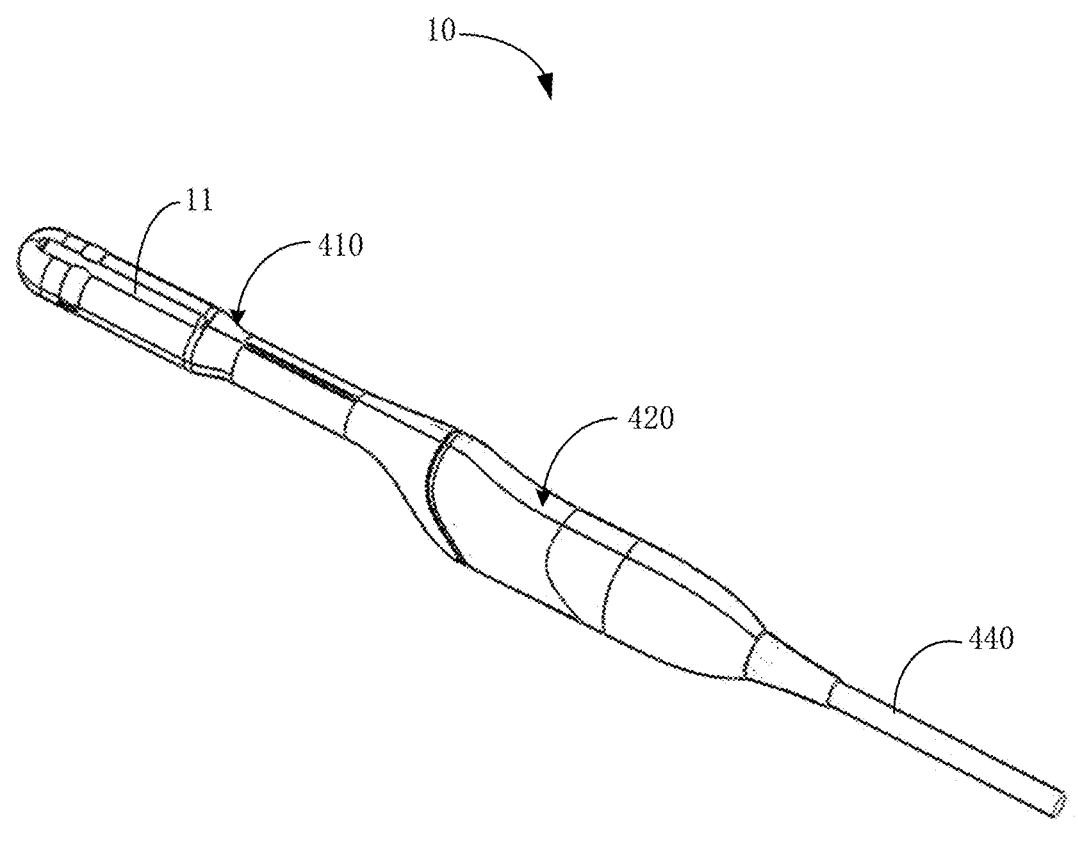
FIG. 1 is a schematic diagram illustrating an ultrasonic probe according to an embodiment of the present disclosure.

10, ultrasonic probe; 11, transducer assembly; 100, convex array; 101, FOV boundary; 110, first lens layer; 111, first bonding surface; 120, first piezoelectric layer; 130, first matching layer; 140, first backing layer; 141, first concave-convex matching portion; 150, first heat dissipation member; 151, second concave-convex matching portion; 200, linear array; 210, second lens layer; 211, second bonding surface; 220, second piezoelectric layer; 230, second matching layer; 240, second backing layer; 241, third concave-convex matching portion; 250, second heat dissipation member; 251, fourth concave-convex matching portion; 300, connecting member; 310, first support section; 311, first screw hole; 320, second support section; 321, second screw hole; 410, shell acoustic head end; 420, shell handle end; 430, electrical connection lead; 440, cable; 450, mainboard.

DETAILED DESCRIPTION OF THE EMBODIMENTS

In order to make the above objectives, features and advantages of the present disclosure more obvious and understandable, specific implementations of the present disclosure are described in detail below with reference to the accompanying drawings. In the following description, many specific details are set forth in order to fully understand the present disclosure. However, the present disclosure can be implemented in many other ways different from those described herein, and those skilled in the art can make similar improvements without departing from the connotation of the present disclosure. Therefore, the present disclosure is not limited by the specific embodiments disclosed below.

In the description of the present disclosure, it should be understood that if the terms "center", "longitudinal", "transverse", "length", "width", "thickness", "upper", "lower", "front", "back", "left", "right", "vertical", "horizontal", "top", "bottom", "inner", "outer", "clockwise", "counterclockwise", "axial", "radial", "circumferential", etc. are used, these terms indicate the orientation or position relationship as shown in the accompanying drawings and are merely intended to facilitate the description of the present disclosure and simplify the description, rather than indicating or implying that the indicated device or element must have a specific orientation or be constructed and operated in a specific orientation. Therefore, these terms are not to be interpreted as limiting the present disclosure.

In addition, if the terms such as "first" and "second" are used, they are used for descriptive purposes only, and should not be understood as indicating or implying relative importance or implicitly indicating the quantity of the technical features indicated. Thus, the features described with "first" and "second", etc., may explicitly or implicitly include at least one of these features. In the description of the present disclosure, if the term "plurality" is used, it means at least two, such as two, three, etc., unless otherwise clearly and specifically defined.

In the present disclosure, unless otherwise clearly specified and limited, if the terms "mounted", "coupling", "connection", "fixation", etc., are used, these terms should be understood in a broad sense, for example, it may be a fixed connection, a detachable connection, or integration. It may be a mechanical connection or an electrical connection. It may be a direct connection or an indirect connection through an intermediate medium. It may be an internal connection between two array elements or an interaction relationship between the two array elements, unless otherwise clearly defined. Those of ordinary skill in the art can understand the specific meanings of the above terms in the present disclosure according to specific situations.

In the present disclosure, unless otherwise clearly specified and limited, if there is a description that a first feature is "on" or "under" a second feature, etc., it may mean that the first and second features are in direct contact, or the first and second features are in indirect contact through an intermediate medium. Moreover, the first feature being "on", "above", or "over" the second feature may mean that the first feature is directly above or obliquely above the second feature, or simply means that the horizontal height of the first feature is greater than that of the second feature. The first feature being "under", "beneath" and "below" the second feature may mean that the first feature is directly below or obliquely below the second feature, or simply means that the horizontal height of the first feature is less than the that of second feature.

It should be noted that when an element is referred to as being "fixed on" or "arranged on" another element, it may be directly on the other element or there may be an intervening element. When an element is referred to as being "connected to" another element, it may be directly connected to the other element or there may also be an intermedium element. If present, the terms "vertical", "horizontal", "upper", "lower", "left", "right" and similar expressions used in this disclosure are for the purpose of illustration only and are not meant to be the only implementation methods.

In the related art, an ultrasonic probe is generally consisted of two transducer arrays, including a linear array for longitudinal plane imaging and a convex array for transverse plane imaging. The two transducer arrays are generally arranged in a T-shape, resulting in a blind area in an imaging area. In a case that positions of a punctured tissue and a puncture needle cannot be simultaneously presented in an ultrasonic image, doctors need to frequently move the probe to determine the positions of the punctured tissue and the puncture needle, which affects the detection efficiency.

Based on this, the present disclosure provides an ultrasonic probe that can solve at least one of the above problems. The ultrasonic probe in an embodiment of the present disclosure will be described in detail below with reference to the accompanying drawings.

Figure 2:
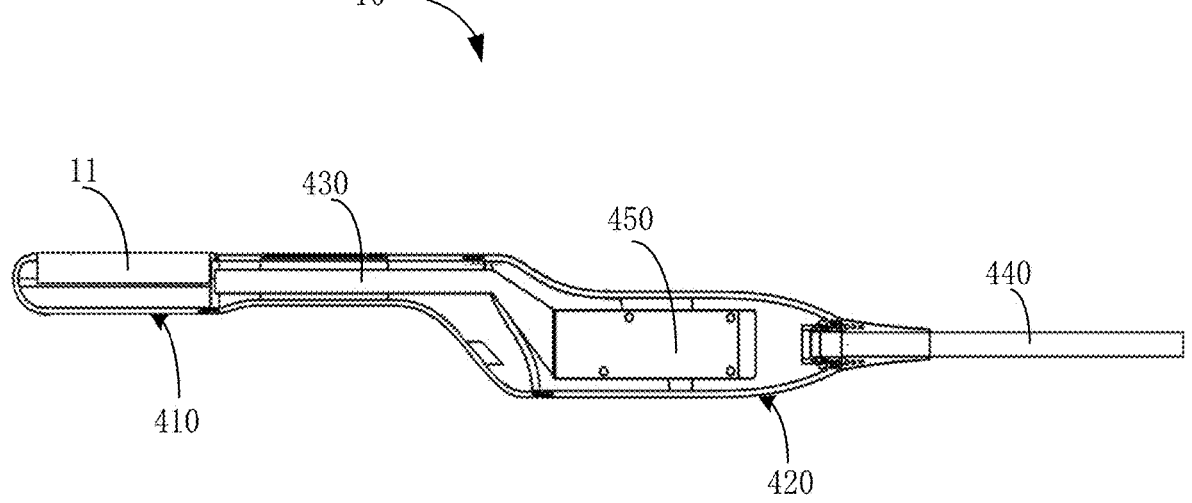
FIG. 2 is a cross-sectional view of the ultrasonic probe shown in FIG. 1.
Figure 3:
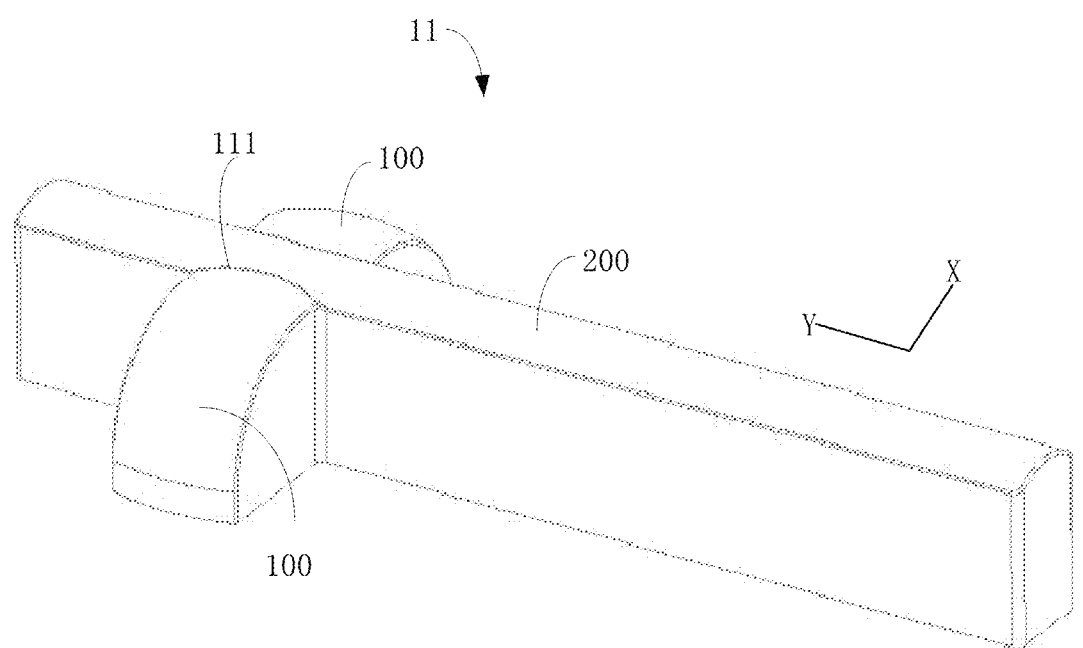
FIG. 3 is a schematic diagram illustrating a transducer assembly in the ultrasonic probe shown in FIG. 1.
Figure 4:
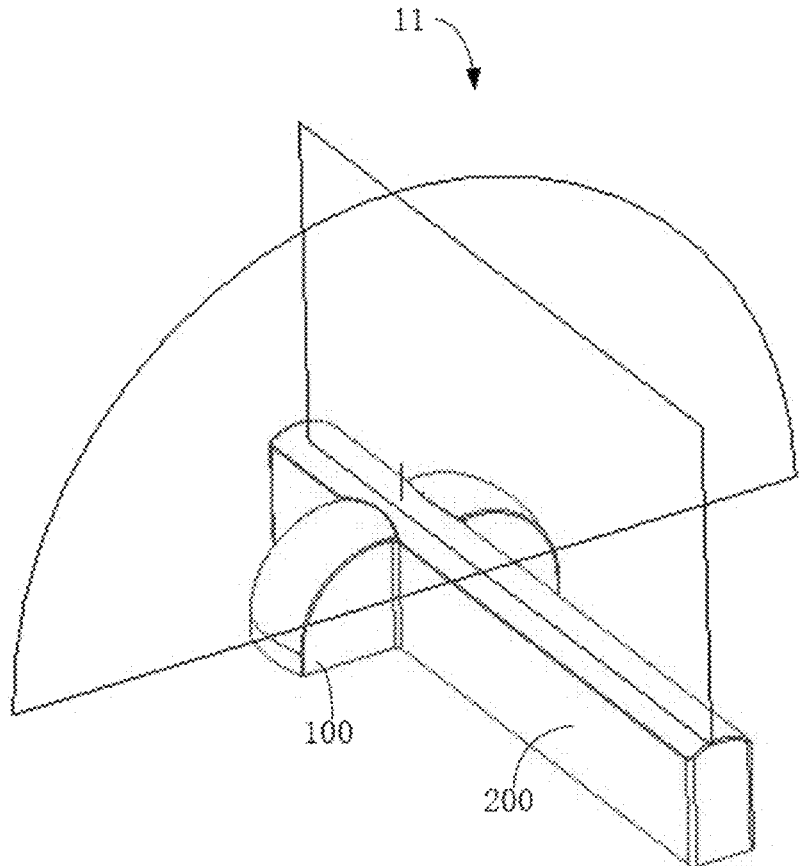
FIG. 4 is a simplified diagram illustrating an imaging area of the transducer assembly shown in FIG. 3.

Referring to FIGS. 1 to 7, an ultrasonic probe 10 according to an embodiment of the present disclosure includes a transducer assembly 11. The transducer assembly 11 includes a first transducer and a linear array 200. The first transducer includes two convex arrays 100 arranged in a first direction, and the linear array 200 is connected between the two convex arrays 100. An arrangement direction of the linear array 200 is perpendicular to the first direction. As shown in FIG. 3, the first direction is the X direction shown in the figure, and the arrangement direction of the linear array 200 is the Y direction shown in the figure. In some application scenarios, the arrangement direction of the linear array 200 is a forward scanning direction of the ultrasonic probe 10.

The convex arrays 100 are configured to perform coronal plane imaging and the linear array 200 is configured to perform sagittal plane imaging. By performing imaging using both the convex arrays 100 and the linear array 200 simultaneously, information on the two planes of one same body portion can be scanned and observed. Specifically, each of the convex arrays 100 can transmit and receive ultrasonic waves in its own radial direction. After the ultrasonic waves received by the convex arrays 100 are received and processed by a host of an ultrasonic device, an ultrasonic image of a radial area surrounding an outer peripheral surface of the probe may be formed. For example, the convex arrays 100 can detect an inner wall of a cavity and tissues close to the inner wall of the cavity to obtain a coronal plane image, so that a position of a punctured tissue can be observed. The linear array 200 can transmit and receive ultrasonic waves to and from an outer peripheral wall of the ultrasonic probe 10. After the ultrasonic waves received by the linear array 200 are received and processed by the host of the ultrasonic device, an ultrasonic image of a front end area is formed. For example, the linear array 200 can detect the position of the puncture needle to obtain a sagittal plane image. During use, the convex arrays 100 and the linear array 200 transmit and receive ultrasonic waves simultaneously, so that the positions of the punctured tissue and the tip of the puncture needle can be observed simultaneously, without the need for frequently moving the ultrasonic probe 10 to switch between two planes, thereby accurately achieving the intracavitary puncture operation and improving the detection accuracy and efficiency.

It should be noted that the first transducer may be consisted of two independent convex arrays 100, and the two independent convex arrays 100 are not connected to each other. That is, the two convex arrays 100 arranged spaced apart from each other in the first direction Alternatively, a middle part of one convex array may be processed to form a trench in the middle part, and the trench is configured to connect the linear array, such that said one convex array forms an irregular-shaped convex array, and two ends of the irregular-shaped convex array in the first direction form the two convex arrays 100 included in the first transducer as described above. That is, the two convex arrays 100 may connect with each other to form as an integrated structure. The specific configurations can be selected according to actual needs, which is not limited here.

In an embodiment, the ultrasonic probe 10 of the embodiments of the present disclosure can be applicable to intracavitary detection of various organs, for example, transesophageal, trans-vaginal and trans-anal examinations, but is not limited thereto. The ultrasonic probe 10 may also be used to inspect incisions formed on the body, which is not limited here.

In an embodiment, the convex arrays 100 for coronal plane imaging may be made of an array transducer with a plurality of array elements and a preset frequency range, for example, made of an array transducer with 80 array elements and a frequency of 3 MHz to 10 MHz. The array transducer forming the convex arrays 100 may be referred to as a convex array transducer. In the convex array transducer, a distance between two array elements may be within a range of 0.13 mm to 0.2 mm, and an elevation, i.e., a width of a positive end of the array element, is within a range of 5 mm to 6 mm, and a curvature radius of each of the convex arrays 100 may be within a range of 7 mm to 8.5 mm. The linear array 200 for sagittal plane imaging may be made of an array transducer with a plurality of array elements and a preset frequency range, for example, made of an array transducer with 256 array elements and a frequency of 3 MHz to 14 MHz. The array transducer forming the linear array 200 may be referred to as a linear array transducer. In the linear array transducer, a distance between two array elements may be within a range of 0.2 mm to 0.25 mm, and an elevation is within a range of 3 mm to 5 mm. The convex array transducer and the linear array transducer may each be a 1.5D array or a 1.75D array, etc. In other embodiments, the convex array transducer and the linear array transducer may also each have 96 array elements or 192 array elements, etc. Taking a row of array elements in the transducer as an example, an arrangement direction of the plurality of array elements of the linear array 200 is the same as a length direction of the linear array 200, and an arrangement direction of the plurality of array elements of the convex arrays 100 is perpendicular to the arrangement direction of the plurality of array elements of the linear array 200. In other embodiments, two rows of array elements, a plurality of rows of array elements, etc. may also be arranged in the transducer. The number of array elements of the convex array transducer and the number of array elements of the linear array transducer may be determined according to the size and imaging requirement of the convex arrays 100 and the size and imaging requirement of the linear array 200. The preset frequency range of the convex array transducer and the preset frequency range of the linear array transducer may be determined according to usage needs.

Figure 11:
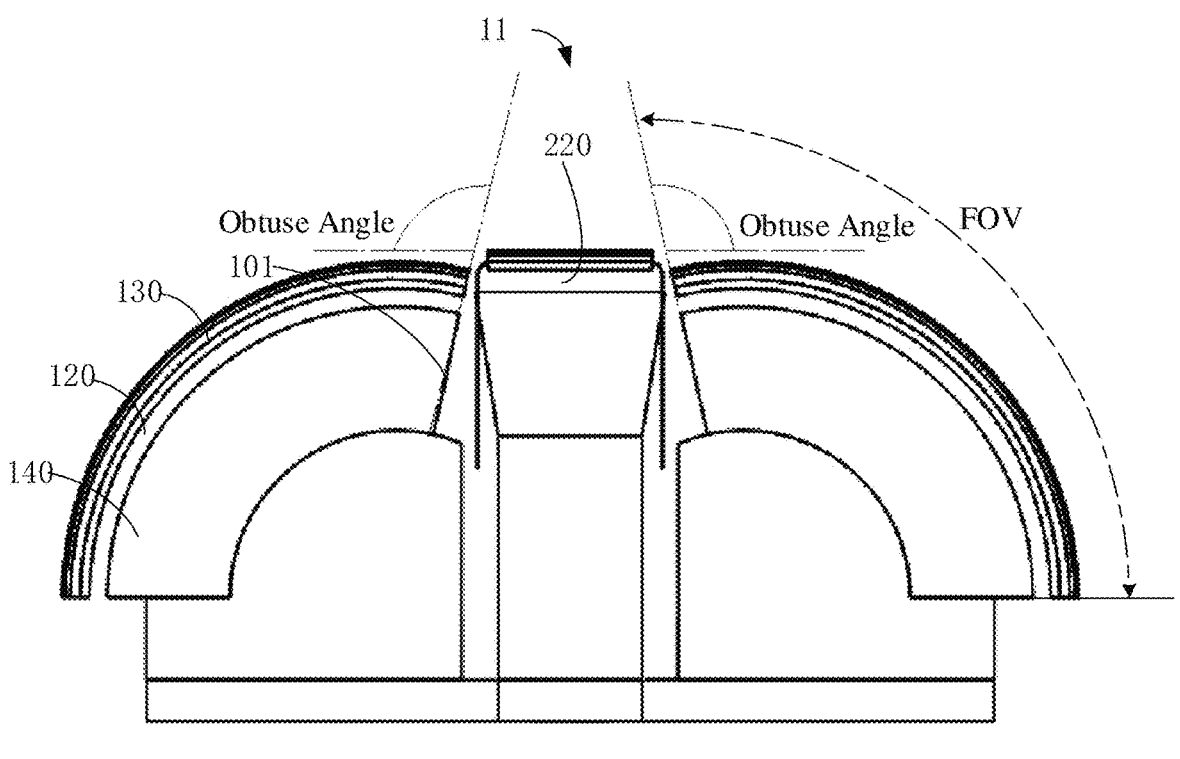
FIG. 11 is a schematic diagram illustrating a transducer assembly in an ultrasonic probe according to a third embodiment of the present disclosure.
Figure 12:
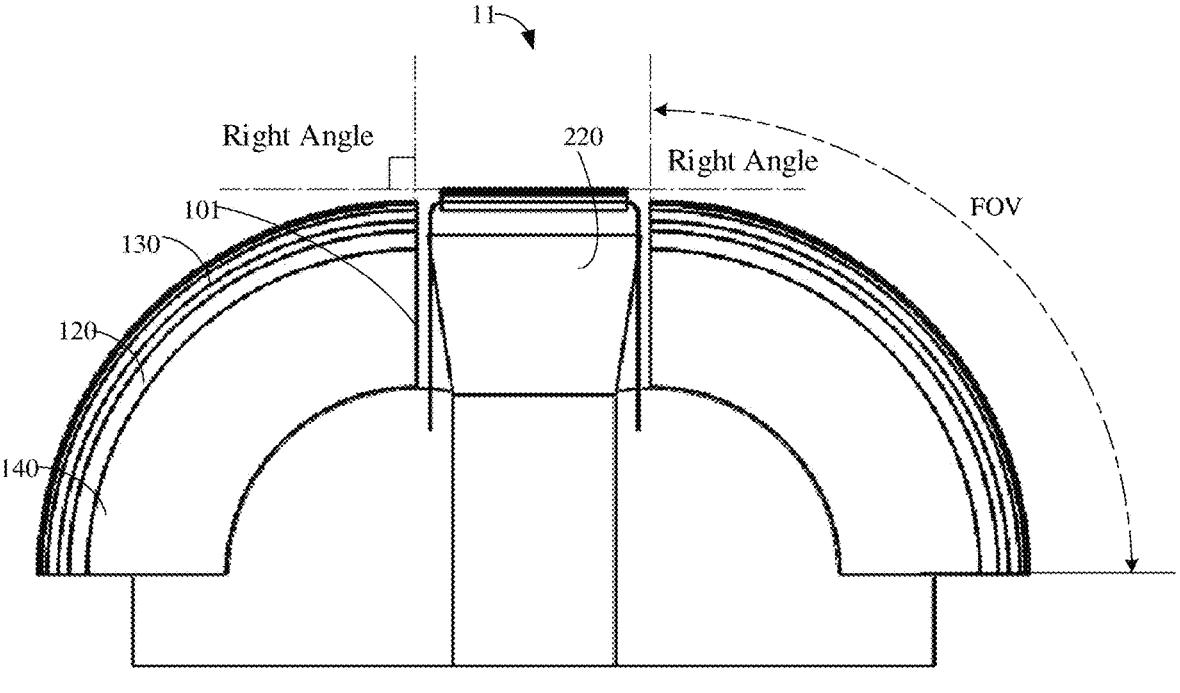
FIG. 12 is a schematic diagram illustrating a transducer assembly in an ultrasonic probe according to a fourth embodiment of the present disclosure.
Figure 13:
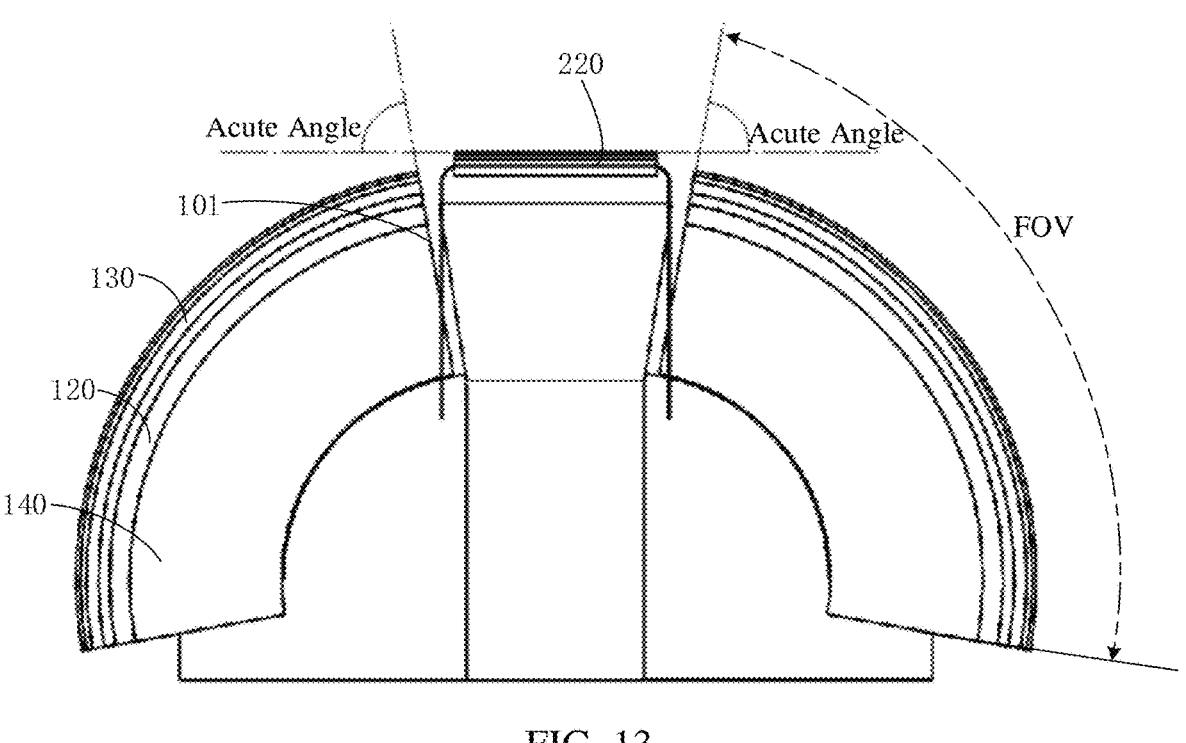
FIG. 13 is a schematic diagram illustrating a transducer assembly in an ultrasonic probe according to a fifth embodiment of the present disclosure.

As shown in FIG. 11, in some embodiments, a field of view (FOV) angle of each of the convex arrays 100 is an obtuse angle. The field of view angle is an angle between a plane where a second piezoelectric layer 220 of the linear array 200 is located and a FOV boundary 101 of the convex array 100, and the boundary 101 refers to a lateral side of the convex array 100 facing the linear array 200. Through this arrangement, it is ensured that an imaging plane of the convex arrays 100 and an imaging plane of the linear array 200 have a sufficient intersection area therebetween. Furthermore, the reliability of simultaneously observing the positions of the punctured tissue and the tip of the puncture needle through the intersection area is ensured, thereby improving the detection accuracy. Since there is no need to frequently move the ultrasonic probe 10, the detection efficiency is also improved. In other embodiments, as shown in FIG. 12, the field of view angle of each of the convex arrays 100 may also be a right angle. In another embodiment, as shown in FIG. 13, the field of view angle of each of the convex arrays 100 may also be an acute angle. The specific form can be set according to actual use requirements and is not limited here.

Figure 5:
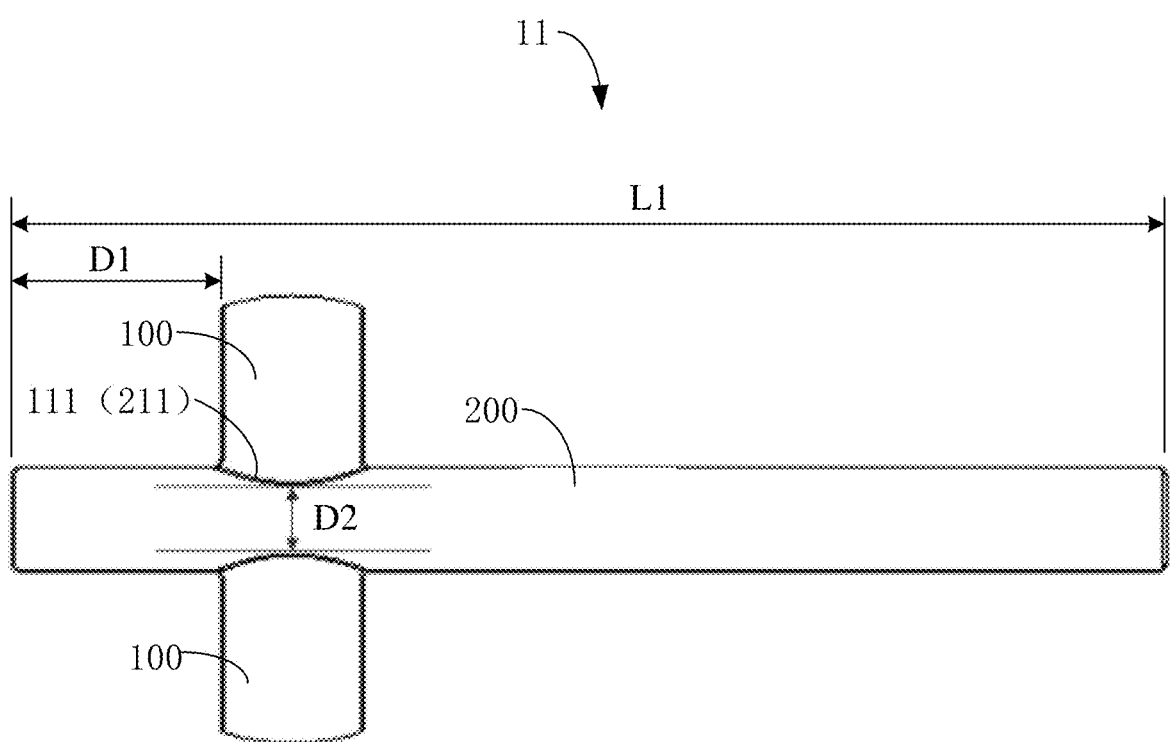
FIG. 5 is a top view of the transducer assembly shown in FIG. 3.

As shown in FIG. 5, in an embodiment, the linear array 200 extends a first distance D1 relative to the convex arrays 100 in a moving direction, and a ratio of the first distance D1 to a length L1 of the linear array 200 is within a range of 0 to 2/3 (excluding 0). In other words, a layout of the linear array 200 and the two convex arrays 100 is in a cross-shaped form. That is, the linear array 200 and the two convex arrays 100 are arranged to form a cross shape. Through this arrangement, it is ensured that an imaging plane of the linear array 200 and an imaging plane of the convex arrays 100 have a sufficient intersection area therebetween. Furthermore, the reliability of simultaneously observing the positions of the punctured tissue and the tip of the puncture needle through the intersection area is ensured, thereby improving the detection accuracy and detection efficiency. Preferably, the ratio of the first distance D1 that the linear array 200 extends relative to the convex arrays 100 to the length L1 of the linear array 200 is within a range of 0 to 1/2 (excluding 0). More preferably, the ratio of the first distance D1 that the linear array 200 extends relative to the convex arrays 100 to the length L1 of the linear array 200 is within a range of 1/4 to 1/2.

Referring to FIGS. 1 to 7, in an embodiment, each of the convex arrays 100 includes a first lens layer 110, and the first lens layer 110 has a first bonding surface 111. The linear array 200 includes a second lens layer 210, and the second lens layer 210 has a second bonding surface 211 connected to the first bonding surface 111. Ultrasonic beams emitted by the convex arrays 100 and the linear array 200 are focused by the first lens layers 110 and the second lens layer 210, respectively. The first bonding surface 111 and the second bonding surface 211 are connected to each other, thereby improving a sealing effect of the transducer assembly 11. Furthermore, the two first lens layers 110 may be in an integrated structure. In this way, the sealing surfaces to be assembled can be reduced, thereby reducing the hidden dangers caused by sealing failure. Meanwhile, the errors occur during the assembly process can be reduced. In addition, a blind area of a coronal imaging area can be reduced, thereby increasing the accuracy of imaging detection.

As shown in FIGS. 1 to 7, in an embodiment, the two convex arrays 100 are symmetrically arranged on both sides of the linear array 200, and an orientation of the first bonding surface 111 is in conformity with an orientation of the second bonding surface 211 located on a same side. For example, the first bonding surface 111 and the second bonding surface 211 are each a cambered surface. In this way, the coronal imaging area of the convex arrays 100 and the sagittal imaging area of the linear array 200 can intersect with each other, i.e., there is an orthogonal plane between the coronal plane and the sagittal plane. Since the convex arrays 100 and the linear array 200 transmit and receive ultrasonic waves simultaneously during use, information of the orthogonal plane can be displayed on the same imaging plane. Therefore, during the puncture process, the doctor can simultaneously observe the positions of the punctured tissue and the tip of the puncture needle through the orthogonal plane, without no need for frequently moving the ultrasonic probe 10 to switch between the two planes, thereby accurately achieving the intracavitary puncture operation and improving the detection accuracy and detection efficiency. The first bonding surface 111 and the second bonding surface 211 may be bonded together by using an adhesive.

As shown in FIGS. 1 to 7, in another embodiment, in order to enhance the acoustic performance, a distance between the first bonding surfaces 111 of the two convex arrays 100 gradually decreases first and then gradually increases in the arrangement direction of the linear array 200, i.e., when viewed from the perspective of each of the convex arrays 100, the first bonding surface 111 is an outwardly convex cambered surface, so as to facilitate the acoustic focusing. It can be understood that the second bonding surface 211 of the linear array 200 matches a shape of the first bonding surface 111 of the convex array 100. In this way, the transitions between the linear array 200 and the convex arrays 100 can be more smoot, and it is not easy to hide dirt, and it is easy to clean.

As shown in FIG. 5, in an embodiment, a minimum distance D2 between the two first bonding surfaces 111 is greater than the elevation of the linear array 200, so as to ensure that the coronal plane imaged by the convex arrays and the sagittal plane imaged by the linear array have an intersection area therebetween, thereby ensuring the usage reliability of the ultrasonic probe 10.

Figure 6:
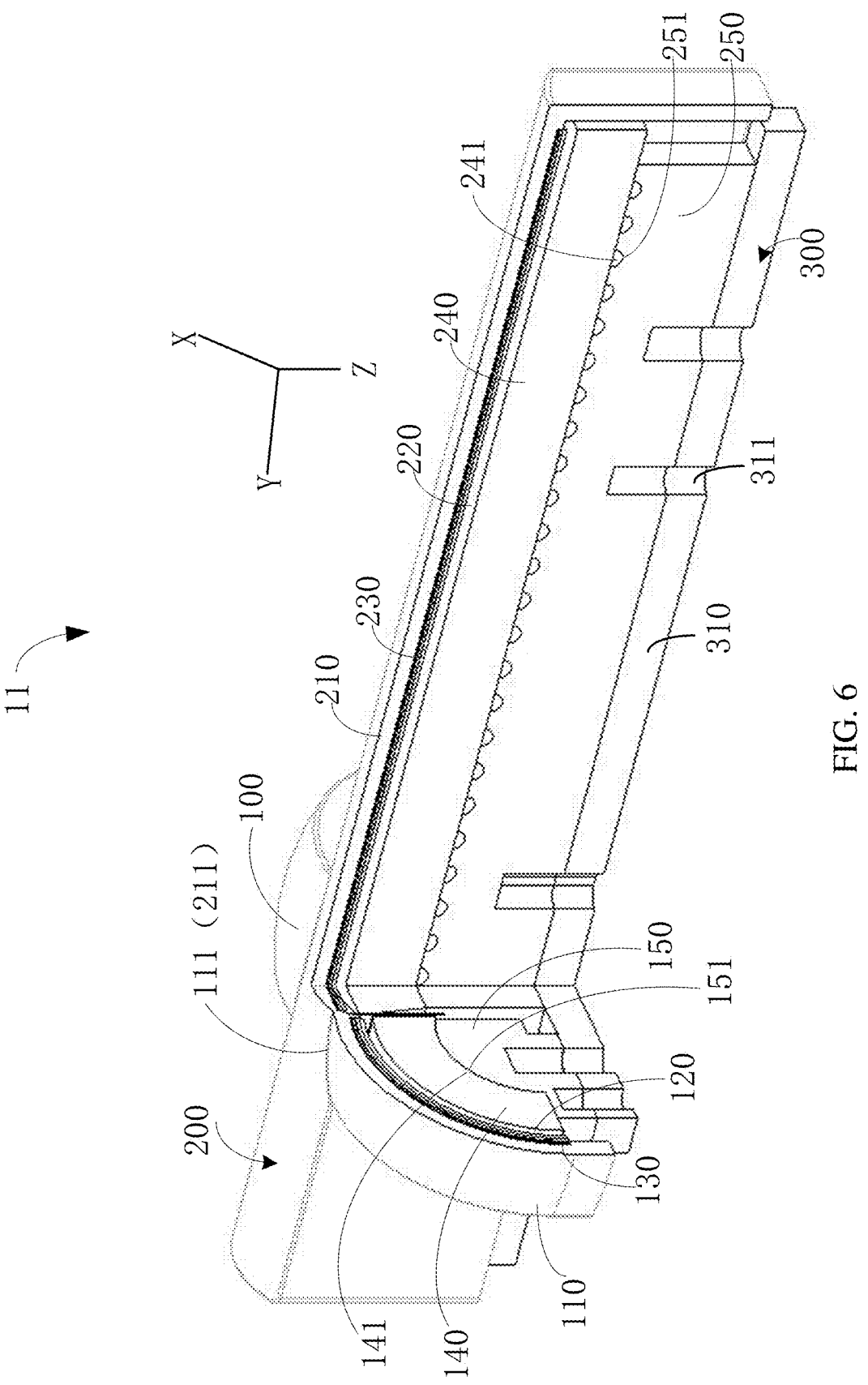
FIG. 6 is a partial cross-sectional view of the transducer assembly shown in FIG. 3.
Figure 7:
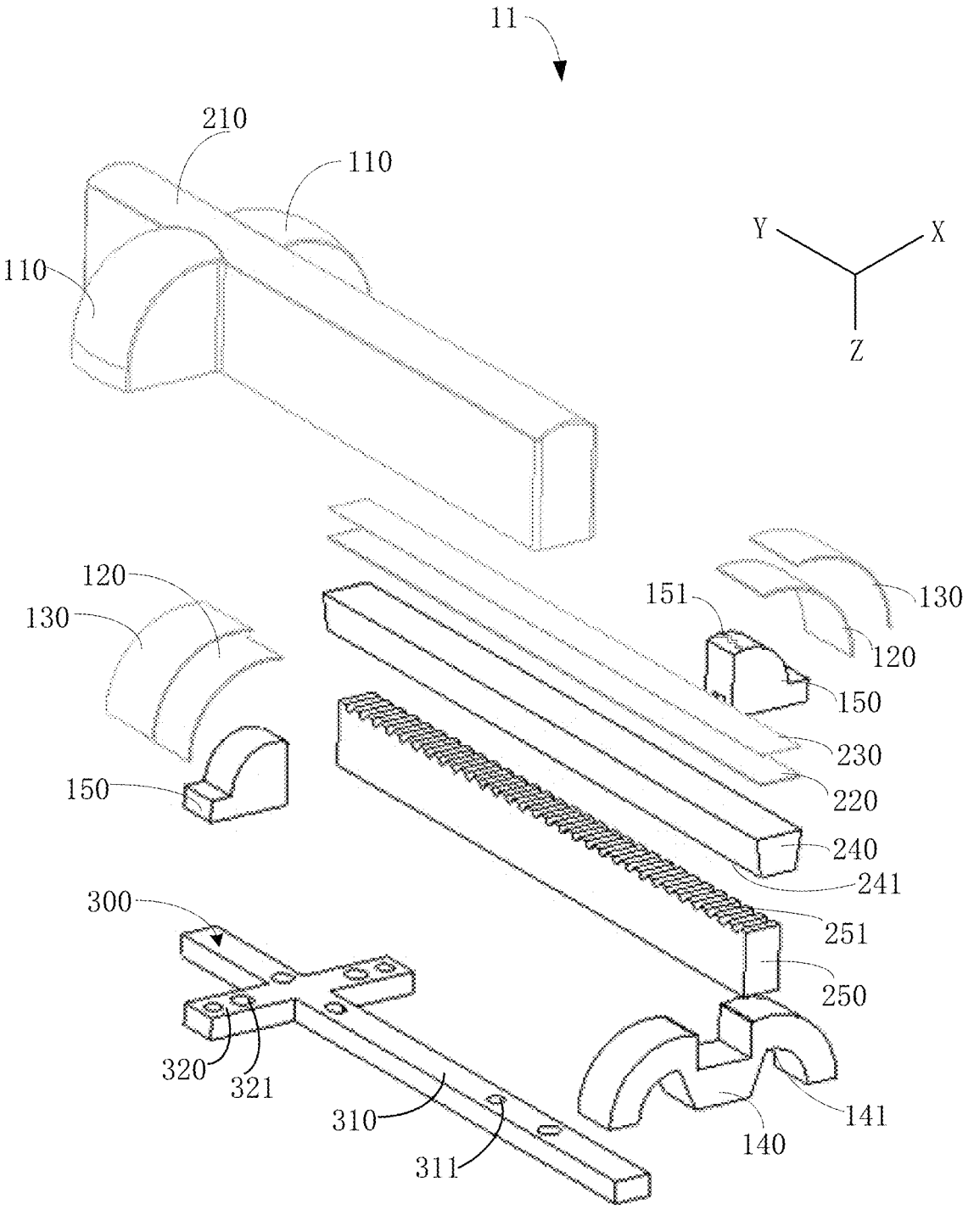
FIG. 7 is an exploded view of the transducer assembly shown in FIG. 3.
Figure 8:
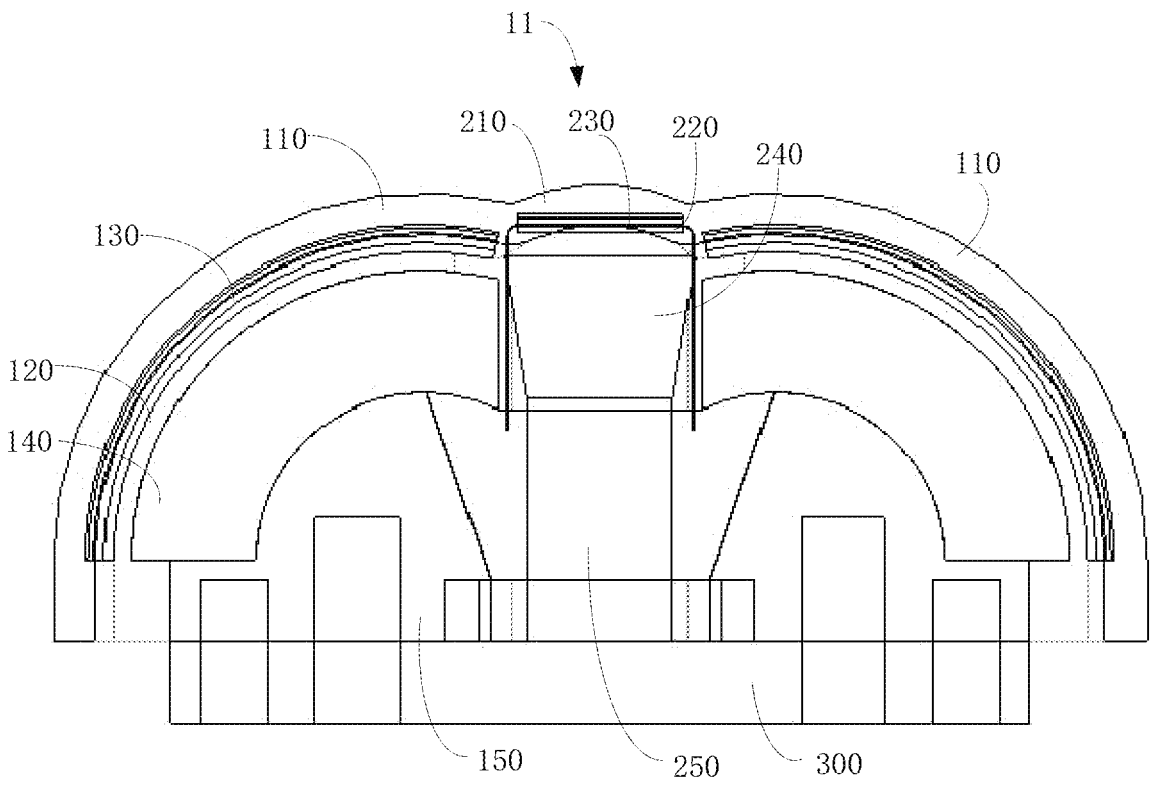
FIG. 8 is a cross-sectional view of the transducer assembly shown in FIG. 3.

As shown in FIGS. 6 to 8, in an embodiment, the first lens layers 110 and the second lens layer 210 are in an integrated structure. By manufacturing the lens layers of the linear array 200 and the two convex arrays 100 in an integrated structure, the sealing surfaces to be assembled can be reduced, thereby reducing the hidden danger caused by sealing failure. Meanwhile, the errors occur during the assembly process can be reduced. In addition, an imaging blind area can be also reduced, thereby increasing the accuracy of imaging detection.

As shown in FIGS. 6 to 8, in an embodiment, each of the convex arrays 100 further includes a first piezoelectric layer 120 stacked with the first lens layer 110 in a second direction. The linear array 200 further includes a second piezoelectric layer 220 stacked with the second lens layer 210 in the second direction. As shown in FIG. 6, the second direction is indicated by the Z direction. It can be understood that the second direction, the first direction and the arrangement direction of the linear array 200 are perpendicular to each other for every two of them. The first piezoelectric layer 120 and the second piezoelectric layer 220 are each configured to perform electroacoustic conversion, and are each a pipe part of the transducer. They convert an electrical signal excited by an ultrasonic system into ultrasonic waves. After entering the human body, the ultrasonic waves reflected at different tissue boundaries are converted into electrical signals by the piezoelectric layers and provided to the ultrasonic host for processing. The positive and negative surfaces of each of the first piezoelectric layers 120 and the second piezoelectric layer 220 are respectively coated with a conductive material to enhance the effect of the electroacoustic conversion. A bonding surface between the first piezoelectric layer 120 and the second piezoelectric layer 220 is a plane, and the first piezoelectric layer 120 and the second piezoelectric layer 220 may be bonded by using an adhesive.

As shown in FIGS. 6 to 8, in an embodiment, each of the convex arrays 100 further includes a first matching layer 130 stacked between the first lens layer 110 and the first piezoelectric layer 120. The linear array 200 further includes a second matching layer 230 stacked between the second lens layer 210 and the second piezoelectric layer 220. The first matching layer 130 and the second matching layer 230 are provided to cooperate with the first piezoelectric layer 120 and the second piezoelectric layer 220, respectively, so as to achieve acoustic matching. A bonding surface between the first matching layer 130 and the second matching layer 230 is a plane, and the first matching layer 130 and the second matching layer 230 may be bonded by using an adhesive.

As shown in FIGS. 6 to 8, in an embodiment, each of the convex arrays 100 further includes a first backing layer 140 stacked on a side of the first piezoelectric layer 120 facing away from the first matching layer 130. The linear array 200 further includes a second backing layer 240 stacked on a side of the second piezoelectric layer 220 facing away from the second matching layer 230. The first backing layer 140 and the second backing layer 240 are configured to support and absorb ultrasound for the first piezoelectric layer 120 and the second piezoelectric layer 220, respectively. The lens layers, the matching layers, and the backing layers may each be formed by casting. The lens layers may each be made of various materials suitable for making an acoustic lens, such as polyethylene synthetic resin, or the like. A bonding surface between the first backing layer 140 and the second backing layer 240 is a plane, and the first backing layer 140 and the second backing layer 240 may be bonded by using an adhesive.

As shown in FIGS. 6 to 8, in an embodiment, each of the convex arrays 100 further includes a first heat dissipation member 150 connected to the first backing layer 140. The linear array 200 further includes a second heat dissipation member 250 connected to the second backing layer 240. The first heat dissipation members 150 and the second heat dissipation member 250 are provided to dissipate heat from the ultrasonic probe 10, thereby reducing the possibility of discomfort to the human body caused by excessive temperature. The first heat dissipation members 150 and the second heat dissipation member 250 may each be made of a metal heat dissipation material such as aluminum alloy, copper

Figures 9, 10:
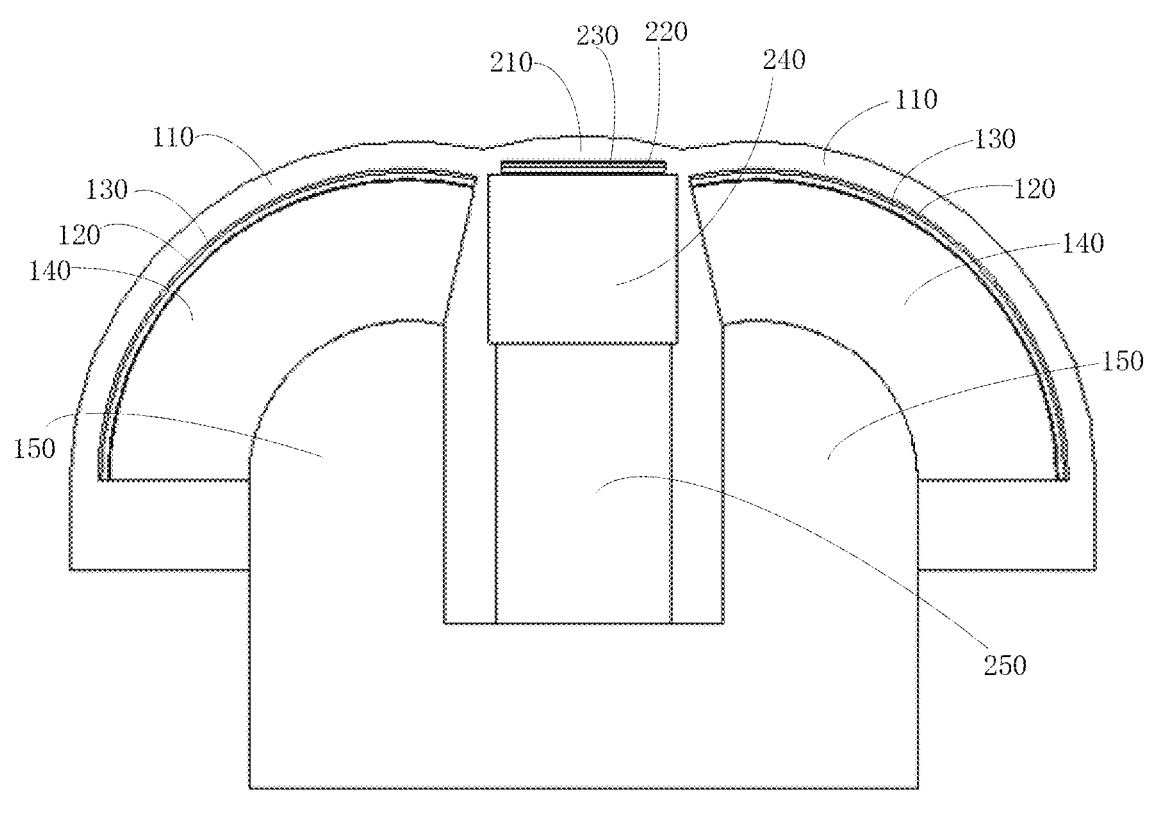
FIG. 9 is a cross-sectional view of the transducer assembly according to another embodiment of the present disclosure.
FIG. 10 is a schematic diagram illustrating a transducer assembly in an ultrasonic probe according to a second embodiment of the present disclosure.

10 alloy, or the like, or may be made of a heat-conductive non-metallic material such as graphene. In FIGS. 6 to 8, the two first heat dissipation members 150 and the second heat dissipation member 250 are each manufactured in a separate manner. However, as shown in FIG. 9, in some other embodiments, some or all of the two first heat dissipation members 150 and the second heat dissipation member 250 may be manufactured in an integrated structure. For example, see FIG. 9, in the example of FIG. 9, the two first heat dissipation members 150 are manufactured in an integrated structure, while the second heat dissipation member 250 is manufactured in a separate manner from the first heat dissipation members 150 in the integrated structure. In this way, the sealing surfaces to be assembled can be reduced, and the errors occur during the assembly process can be reduced.

As shown in FIGS. 6 to 8, in an embodiment, the first heat dissipation member 150 is connected to a side of the first backing layer 140 facing away from the first matching layer 130. In other words, the first backing layer 140 and the first heat dissipation member 150 are arranged in the second direction (Z direction in the figure). In this way, in addition to the heat dissipation and cooling effect, the first heat dissipation member 150 can also cooperate with the first backing layer 140 to further provide a good support effect for the first piezoelectric layer 120. In addition, by arranging the first heat dissipation member 150 below the first backing layer 140, a space occupied by the first heat dissipation member 150 and the first backing layer 140 in the first direction can be reduced, making the layout of the entire ultrasonic probe 10 more compact.

It can be understood that in other embodiments, the first heat dissipation member may be connected to a side of the first backing layer in the first direction, and the second heat dissipation member may be connected to a side of the second backing layer in the first direction.

As shown in FIG. 6 and FIG. 7, in an embodiment, the first backing layer 140 and the first heat dissipation member 150 are provided with a first concave-convex matching portion 141 and a second concave-convex matching portion 151 configured to engage with the first concave-convex matching portion 141, respectively. Taking the first heat dissipation member 150 as an example, surfaces between the first heat dissipation member 150 and the first backing layer 140 being in contact with each other are each designed as a concave-convex surface, so that after the first heat dissipation member 150 and the first backing layer 140 are stacked, the contact surfaces thereof are engaged with each other, i.e., a contact area between the first heat dissipation member 150 and the first backing layer 140 is relatively increased, so that it is not easy for the first heat dissipation member 150 and the first backing layer 140 to displace or slide relative to each other. In this way, not only a bonding effect between the first heat dissipation member 150 and the first backing layer 140 is increased, but also the reflection interface can be reduced, the reflection of the ultrasonic waves at a rear end of the ultrasonic probe 10 can be reduced, and the interferences can be reduced.

Specifically, the first concave-convex matching portion 141 provided on the first backing layer 140 is a clamping protrusion, and the second concave-convex matching portion 151 provided on the first heat dissipation member 150 is a clamping groove. Through the cooperation between the clamping protrusion and the clamping groove, the first backing layer 140 is closely connected to the first heat dissipation member 150, so that the first backing layer 140 and the first heat dissipation member 150 are not easily displaced relative to each other.

In another specific embodiment, the clamping protrusion and the clamping groove are each in a regular shape. For example, as shown in FIG. 7, a cross section of the clamping groove is triangular. Correspondingly, a shape of the clamping protrusion is adapted to a shape of the clamping groove, i.e., the shape of the clamping protrusion is a cone, and the cone can be a circular cone or a pyramid, so that the clamping protrusion and the clamping groove can be engaged with each other. In other embodiments, the shape of the clamping protrusion may be a cylinder, a cube or a cuboid. It can be understood that the shape of the clamping protrusion is not limited thereto, and the shape of the clamping protrusion may also be in an irregular shape.

Further, as shown in FIGS. 6 and 7, in another embodiment, the second backing layer 240 and the second heat dissipation member 250 are provided with a third concave-convex matching portion 241 and a fourth concave-convex matching portion 251 configured to engage with the third concave-convex matching portion 241, respectively. Through this arrangement, a connection effect between the second heat dissipation member 250 and the second backing layer 240 is increased. The second heat dissipation member 250 is connected to a side of the second backing layer 240 facing away from the second matching layer 230. Through this arrangement, after the second heat dissipation member 250 and the second backing layer 240 are stacked, the contact surfaces thereof are engaged with each other, i.e., a contact area between the second heat dissipation member 250 and the second backing layer 240 is relatively increased, so that it is not easy for the second heat dissipation member 250 and the second backing layer 240 to displace or slide relative to each other, thereby increasing a bonding effect between the second heat dissipation member 250 and the second backing layer 240. Moreover, the reflection interface can be reduced, the reflection of the ultrasonic waves at a rear end of the ultrasonic probe 10 can be reduced, and the interferences can be reduced.

As shown in FIGS. 6 to 8, the two first backing layers 140 are in an integrated structure. By manufacturing the backing layers of the two convex arrays 100 in an integrated manner, the errors occur during the assembly of the two convex arrays 100 is reduced, thereby ensuring that the two convex arrays 100 are imaged on a same plane, so as to improve the accuracy of imaging. As shown in FIG. 10, in another embodiment, the two first backing layers 140 may be manufactured in a separate manner.

As shown in FIGS. 6 to 8, in an embodiment, the ultrasonic probe 10 further includes a connecting member 300, and the linear array 200 and the convex arrays 100 are each connected to the connecting member 300. The linear array 200 and the convex arrays 100 are positioned and fixed by the connecting member 300 to ensure the accuracy of positioning. In another embodiment, the ultrasonic probe 10 may not have the connecting member 300. Instead, the linear array 200 and the convex arrays 100 may be directly connected and positioned relative to each other, or the linear array 200 and the convex arrays 100 may each be connected to a housing so that the linear array 200 and the convex arrays 100 can be positioned and fixed by the housing.

Further, as shown in FIG. 7, the connecting member 300 includes a first support section 310 and second support sections 320 connected to both sides of the first support section 310 in the first direction, i.e., the connecting member 300 is in a cross-shaped sheet structure, so as to be compatible with the arrangement position of the convex arrays

100 and the linear array 200. The first support section 310 and the second support sections 320 may be manufactured in a separate manner or manufactured in an integrated structure. The ultrasonic probe 10 further includes a first fastener and second fasteners. The first fastener is configured to connect the first support section 310 and the linear array 200, and each of the second fastener is configured to connect the second support section 320 and the convex array 100 located on a same side. Specifically, as shown in FIGS. 6 and 7, the first support section 310 and the second heat dissipation member 250 are each provided with a first screw hole 311, and the first fastener is inserted through the first screw holes 311 of the first support section 310 and the second heat dissipation member 250 to achieve the connection between the first support section 310 and the second heat dissipation member 250. The second support section 320 and the first heat dissipation member 150 are each provided with a second screw hole 321, and the second fastener is inserted through the second screw holes 321 of the second support section 320 and the first heat dissipation member 150 to achieve the connection between the second support section 320 and the first heat dissipation member 150. In this way, a connection effect between the components is improved, thereby improving the usage reliability of the ultrasonic probe 10. The first fastener and the second fasteners may be screws, etc. In other embodiments, the first heat dissipation members and the second heat dissipation member may also be bonded to the connecting member by using an adhesive.

In some embodiments, the second support sections 320 are slidably connected to the first support section 310, and can drive the convex arrays 100 to move in the arrangement direction of the linear array 200. In this way, the distance of the linear array 200 relative to the convex array 100 can be easily adjusted, thereby meeting actual use requirements and being more flexible in use.

As shown in FIGS. 1 to 3, in some embodiments, the ultrasonic probe 10 further includes a shell acoustic head end 410, a shell handle end 420, an electrical connection lead 430, a mainboard 450, and a cable 440. The linear array 200 and the convex arrays 100 in the transducer assembly 11 are integrated in the shell acoustic head end 410, and the mainboard 450 is located at the shell handle end 420. The electrical connection lead 430 is configured to achieve an electrical connection between the transducer assembly 11 and the mainboard 450. The cable 440 is configured to connect to the host of the ultrasonic device, so as to realize the input and output of signals, but is not limited thereto. The ultrasonic probe 10 can also be connected to the host in a wireless manner. In the process of inserting the shell acoustic head end 410 into the cavity, in order to improve the comfort of examination and alleviate the pain of the patient, an outer shape of the shell acoustic head end 410 may be configured to be in a cylindrical shape, and a transition area where a diameter changes is designed to be in an arc-shape to form a smooth transition. Since there is no sharp structure such as edges and corners on an outer surface of the ultrasonic probe 10, the patient feels more comfortable during the insertion process. A length, a diameter, and other parameters of the shell acoustic head end 410 may be set to match the cavity to be examined.

Furthermore, an embodiment of the present disclosure further provides an ultrasonic device (not shown), including a host (not shown), a display (not shown), and an ultrasonic probe 10 according to any of the above embodiments. The ultrasonic probe 10 is configured to acquire ultrasonic imaging data. The host is communicatively connected to the ultrasonic probe 10, and is configured to receive and process the ultrasonic imaging data to generate an ultrasonic image. The display is connected to the host, and is configured to display the ultrasonic image.

Taking the application of the ultrasonic probe in intracavitary ultrasonic puncture diagnosis as an example, since the ultrasonic device includes the ultrasonic probe of the embodiment as described above, the doctor can simultaneously observe the positions of the punctured tissue and the tip of the puncture needle through the orthogonal plane during the puncture process, without the need for frequently moving the ultrasonic probe to switch between the two planes, thereby accurately achieving the intracavitary puncture operation and improving the detection accuracy and efficiency.

In addition to the ultrasonic probe, the host and the display device described above, the ultrasonic device of the embodiment of the present disclosure may further include other components, such as a trolley, and these related components can refer to the prior art.

The technical features in the above embodiments may be combined arbitrarily. For concise description, not all possible combinations of the technical features in the above embodiments are described. However, provided that they do not conflict with each other, all combinations of the technical features are to be considered to be within the scope described in this specification.

The above-mentioned embodiments only describe several implementations of the present disclosure, and their description is specific and detailed, but should not be understood as a limitation on the patent scope of the present disclosure. It should be noted that, for a person of ordinary skill in the art may further make variations and improvements without departing from the conception of the present disclosure, and these all fall within the protection scope of the present disclosure. Therefore, the protection scope of the present disclosure should be subject to the appended claims.

What is claimed is:

1. An ultrasonic probe, comprising a transducer assembly, wherein the transducer assembly comprises:

a first transducer comprising two convex arrays arranged in a first direction, each of the two convex arrays comprising a first piezoelectric layer, so that the first transducer comprising two first piezoelectric layers; and a linear array connected between the two convex arrays, and an arrangement direction of the linear array being perpendicular to the first direction;

wherein the two first piezoelectric layers are spaced apart from each other and located on two sides of the linear array in the first direction.

2. The ultrasonic probe according to claim 1, wherein a field of view angle of each of the two convex arrays is an obtuse angle, such that an intersection area exists between an imaging plane of each of the two convex arrays and an imaging plane of the linear array.

3. The ultrasonic probe according to claim 1, wherein the linear array and the two convex arrays are arranged to form a cross shape; and/or wherein the linear array comprises a second piezoelectric layer, and the second piezoelectric layer is located between the two first piezoelectric layers in the first direction, so that the two first piezoelectric layers are spaced apart from each other by the second piezoelectric layer in the first direction.

4. The ultrasonic probe according to claim 1, wherein the linear array extends a first distance relative to each of the two convex arrays in the arrangement direction of the linear array, and a ratio of the first distance to a length of the linear array is higher than 0 and less than or equal to 2/3.

5. The ultrasonic probe according to claim 3, wherein the ratio of the first distance to the length of the linear array is higher than or equal to 1/4 and less than or equal to 1/2.

6. The ultrasonic probe according to claim 1, wherein each of the two convex arrays comprises a first lens layer, and the first lens layer has a first bonding surface; and wherein the linear array comprises a second lens layer, and the second lens layer has second bonding surfaces connected to the first bonding surfaces.

7. The ultrasonic probe according to claim 6, wherein an orientation of each of the first bonding surfaces is in conformity with an orientation of one of the second bonding surfaces located on a same side.

8. The ultrasonic probe according to claim 7, wherein the first bonding surfaces and the second bonding surfaces are each a cambered surface.

9. The ultrasonic probe according to claim 7, wherein a distance between the first bonding surfaces of the two convex arrays gradually decreases first and then gradually increases in the arrangement direction of the linear array.

10. The ultrasonic probe according to claim 9, wherein a minimum distance between the two first bonding surfaces is greater than an elevation of the linear array.

11. The ultrasonic probe according to claim 6, wherein each of the two first piezoelectric layers is stacked with a corresponding first lens layer in a second direction;

each of the two convex arrays further comprises a first matching layer arranged between a corresponding first lens layer and a corresponding first piezoelectric layer;

each of the two convex arrays further comprises a first backing layer stacked on a side of a corresponding first piezoelectric layer facing away from a corresponding first matching layer;

the linear array further comprises a second piezoelectric layer stacked with the second lens layer in the second direction;

the linear array further comprises a second matching layer arranged between the second lens layer and the second piezoelectric layer; and the linear array further comprises a second backing layer stacked on a side of the second piezoelectric layer facing away from the second matching layer, and the second direction, the first direction, and the arrangement direction of the linear array are perpendicular to each other.

12. The ultrasonic probe according to claim 11, wherein each of the two convex arrays further comprises a first heat dissipation member connected to the first backing layer; and the linear array further comprises a second heat dissipation member connected to the second backing layer.

13. The ultrasonic probe according to claim 12, wherein the first backing layer and the first heat dissipation member are provided with a first concave-convex matching portion and a second concave-convex matching portion configured to engage with the first concave-convex matching portion, respectively; and/or the second backing layer and the second heat dissipation member are provided with a third concave-convex matching portion and a fourth concave-convex matching portion configured to engage with the third concave-convex matching portion, respectively.

14. The ultrasonic probe according to claim 13, wherein the first heat dissipation member is connected to a side of the first backing layer facing away from the first matching layer; and/or the second heat dissipation member is connected to a side of the second backing layer facing away from the second matching layer.

15. The ultrasonic probe according to claim 12, wherein the first heat dissipation member is connected to a side of the first backing layer in the first direction; and/or the second heat dissipation member is connected to a side of the second backing layer in the first direction.

16. The ultrasonic probe according to claim 12, wherein the first lens layer and the second lens layer are in an integrated structure; and/or the two first backing layers are in an integrated structure; and/or the two first heat dissipation members are in an integrated structure.

17. The ultrasonic probe according to claim 1, wherein the ultrasonic probe further comprises a connecting member, and the linear array and each of the two convex arrays are each connected to the connecting member.

18. The ultrasonic probe according to claim 17, wherein the connecting member comprises a first support section and second support sections connected to both sides of the first support section in the first direction;

the ultrasonic probe further comprises a first fastener configured to connect the first support section and the linear array; and the ultrasonic probe further comprises a second fastener configured to connect each of the second support section and one of the convex arrays located on a same side.

19. The ultrasonic probe according to claim 18, wherein each of the second support sections is slidably connected to the first support section, and is capable of driving one of the two convex arrays to move in the arrangement direction of the linear array.

20. An ultrasonic device, comprising:

an ultrasonic probe configured to acquire ultrasonic imaging data, the ultrasonic probe comprising a transducer assembly, wherein the transducer assembly comprises:

a first transducer comprising two convex arrays arranged in a first direction, each of the two convex arrays comprising a first piezoelectric layer, so that the first transducer comprising two first piezoelectric layers; and a linear array connected between the two convex arrays, an arrangement direction of the linear array being perpendicular to the first direction;

wherein the two first piezoelectric layers are spaced apart from each other and located on two sides of the linear array in the first direction;

a host communicatively connected with the ultrasonic probe, and configured to receive and process the ultrasonic imaging data to generate an ultrasonic image; and a display connected to the host, and configured to display the ultrasonic image.

\* \* \* \* \*